(12) United States Patent
Barron et al.

(10) Patent No.: US 10,235,458 B2
(45) Date of Patent: Mar. 19, 2019

(54) AND RELATING TO THE MATCHING OF FORENSIC RESULTS

(75) Inventors: Matthew Barron, Solihull (GB); Richard Livett, Solihull (GB)

(73) Assignee: Eurofins Forensic Services Limited, Teddington, Middlesex (GB)

( * ) Notice: Subject to any disclaimer, the term of this patent is extended or adjusted under 35 U.S.C. 154(b) by 477 days.

(21) Appl. No.: 14/119,629

(22) PCT Filed: May 22, 2012

(86) PCT No.: PCT/GB2012/051159
§ 371 (c)(1),
(2), (4) Date: Nov. 22, 2013

(87) PCT Pub. No.: WO2012/160374
PCT Pub. Date: Nov. 29, 2012

(65) Prior Publication Data
US 2014/0089301 A1    Mar. 27, 2014

(30) Foreign Application Priority Data
May 23, 2011    (GB) .................................. 1108587.5

(51) Int. Cl.
*G16H 50/70* (2018.01)
*G06F 17/30* (2006.01)
*G06F 19/28* (2011.01)

(52) U.S. Cl.
CPC .. *G06F 17/30864* (2013.01); *G06F 17/30867* (2013.01); *G06F 19/28* (2013.01); *G16H 50/70* (2018.01)

(58) Field of Classification Search
CPC ..................... G06F 17/30864; G06F 17/30867
See application file for complete search history.

(56) References Cited

U.S. PATENT DOCUMENTS

| | | | |
|---|---|---|---|
| 8,375,032 B2* | 2/2013 | Birdwell | G06F 17/30442 707/737 |
| 8,429,153 B2* | 4/2013 | Birdwell | G06K 9/6224 707/722 |
| 2002/0007248 A1* | 1/2002 | Gill | G06F 19/18 702/20 |

(Continued)

FOREIGN PATENT DOCUMENTS

| WO | WO 2009/066067 | 5/2009 |
|---|---|---|
| WO | WO 2010/116158 | 10/2010 |

*Primary Examiner* — Jeff A Burke
*Assistant Examiner* — Raheem Hoffler
(74) *Attorney, Agent, or Firm* — Merchant & Gould P.C.

(57) ABSTRACT

A method for comparing DNA containing test results and stored results is provided, including a) a stored result selection and plurality of stored result database creation stage; b) a test result against stored result comparison stage, including: 1) A test result selection and plurality of test result database creation sub-stage; 2) A single test result database against single stored result database search sub-stage, performed for the various pairs of test result databases and stored result databases, to establish matches; 3) An established match review sub-stage, to filter out established matches which do not feature as matches across the other test result against stored result databases; 4) A process outcome sub-stage which provides details of the matches which extend across all the database pairs.

12 Claims, 2 Drawing Sheets

(56) References Cited

U.S. PATENT DOCUMENTS

| | | | | |
|---|---|---|---|---|
| 2003/0044821 A1* | 3/2003 | Bader | ............... | C12Q 1/6883 |
| | | | | 435/6.11 |
| 2008/0234945 A1* | 9/2008 | Walk | ............... | G01N 30/8668 |
| | | | | 702/19 |
| 2009/0132173 A1* | 5/2009 | Puch-Solis | ............ | G06F 19/18 |
| | | | | 702/19 |
| 2009/0277790 A1* | 11/2009 | Asogawa | ............. | G06F 19/18 |
| | | | | 204/455 |
| 2010/0138374 A1* | 6/2010 | Chakraborty | .......... | G06F 19/18 |
| | | | | 706/47 |

* cited by examiner

AND RELATING TO THE MATCHING OF FORENSIC RESULTS

This application is a National Stage Application of PCT/GB2012/051159, filed 22 May 2012, which claims benefit of Serial No. 1108587.5, filed 23 May 2011 in the United Kingdom and which applications are incorporated herein by reference. To the extent appropriate, a claim of priority is made to each of the above disclosed applications.

This invention is concerned with improvements in and relating to matching of results, and, in particular, but not exclusively, to matching a test result, from the analysis of a DNA sample, to one or more stored results.

In many situations, particularly in forensic science, there is a need to consider one piece of evidence against one or more other pieces of evidence.

For instance, it may be desirable to compare a sample collected from a crime scene with a sample collected from a person, with a view to linking the two by comparing the characteristics of their DNA. This is an evidential consideration. The outcome may be used directly in criminal or civil legal proceedings. Such situations include instances where the sample from the crime scene is contributed to by more than one person.

In other instances, it may be desirable to establish the most likely matches between the test sample and stored samples, for instance stored on a database. The most likely matches or links suggested may guide further investigations. This is an intelligence consideration.

In both of these instances, it is desirable to be able to express the strength or likelihood of the comparison made, a so called likelihood ratio, particularly for an evidential consideration or a probability for an intelligence consideration.

When making the comparison, particularly in the intelligence consideration scenario, recent developments have significantly increased the amount of data within a data set that represents a result. This is true for both test results and stored results. The large amount of data and the enormous number of results on a database, for instance, can give rise to computational problems in terms of resources and/or time.

The present invention has amongst its possible aims to provide improved matching of results. The present invention has amongst its possible aims to reduce the computational problems with applying matching logic to the larger data sets.

According to a first aspect of the invention there is provided a method of analysing a test sample against a stored result for another sample, wherein:

the test sample is analysed, the analysis producing a test result, the test result including a test result data set;

the test result data set is processed, by a computer implemented step, to split the test result data set into a plurality of parts, one of the parts being processed to give a first test result database and another of the parts being separately processed to give a second test results database;

a plurality of stored results are obtained, the stored results each including a stored result data set;

the stored result data sets are processed, by a computer implemented step, to split the stored results data set into a plurality of parts, one of the parts being processed to give a first stored results database and another of the parts being separately processed to give a second stored results database;

comparing, in a computer implemented step, one or more entries in the first test result database with one or more entires in the first stored result database to determine whether there is a match between the one or more of the entires in the first test result database and the one or more entires in the first stored results database, and forming a first match list for those matching entries;

comparing, in a computer implemented step, one or more entires in the second test result database with one or more entires in the second stored result database to determine whether there is a match between the one or more of the entries in the second test result database and the one or more entries in the second stored results database, and forming a second match list for those matching entries;

comparing, in a computer implemented step, one or more items on the first match list with one or more items on the second match list to determine whether there is a match between the one or more items in the first match list and the one or more items in the second match list, and forming a first further match list for those matching items;

providing a process outcome from the first further match list, directly or indirectly, the process outcome in form of one or more of the stored results being a potential match with the test result.

According to a second aspect of the invention there is provided a method of analysing a test sample against a stored result for another sample, wherein:

the test sample is analysed, the analysis producing a test result, the test result including a test result data set;

the test result data set is processed to give one or more test result databases;

a plurality of stored results are obtained, the stored results each including a stored result data set;

the stored result data sets being processed to give one or more stored result databases; and comparing one or more entries in one or more of the test result databases with one or more entries in one or more of the stored result databases to inform on one or more of the stored results being a potential match with the test result.

The method may provide that the test result data set is processed, by a computer implemented step. The method may provide that the test result data set is processed to split the test result data set into a plurality of parts. The method may provide that one of the parts is processed to give a first test result database and another of the parts is separately processed to give a second test results database.

The method may provide that the stored result data sets are processed, by a computer implemented step. The method may provide that the stored result data sets are processed to split the stored result data sets into a plurality of parts. The method may provide that one of the parts is processed to give a first stored results database and another of the parts is separately processed to give a second stored results database.

The method may provide for comparing, in a computer implemented step, one or more entries in the first test result database with one or more entires in the first stored result database, preferably to determine whether there is a match between the one or more of the entires in the first test result database and the one or more entires in the first stored results database. The method may provide for forming a first match list for those matching entries.

The method may provide for comparing, in a computer implemented step, one or more entires in the second test result database with one or more entires in the second stored result database, preferably to determine whether there is a match between the one or more of the entries in the second test result database and the one or more entries in the second stored results database. The method may provide for forming a second match list for those matching entries.

The method may provide for comparing, in a computer implemented step, one or more items on the first match list with one or more items on the second match list, preferably to determine whether there is a match between the one or more items in the first match list and the one or more items in the second match list. The method may provide for forming a first further match list for those matching items.

The method may provide a process outcome from the first further match list, directly or indirectly. The method may provide that the process outcome is in the form of one or more of the stored results being a potential match with the test result.

The first and/or second aspects of the invention may include the following features, options or possibilities or those set out elsewhere in this document.

The test sample may be a sample from an unknown source. The test sample may be a sample from a known source, particularly a known person.

The test sample may be contributed to by a single source. The test sample may be contributed to by an unknown number of sources. The test sample may be contributed to by two or more sources. One or more of the two or more sources may be known, for instance the victim of the crime.

The test sample may be analysed to provide evidence, for instance in civil or criminal legal proceedings. The evidence may be as to the relative likelihoods, a likelihood ratio, of one hypothesis to another hypothesis. In particular, this may be a hypothesis advanced by the prosecution in the legal proceedings and another hypothesis advanced by the defence in the legal proceedings.

The test sample may be analysed in an intelligence gathering method, for instance to provide information to further investigative processes, such as evidence gathering. The test sample may be analysed to establish a list of stored results which are the most likely matches with the test sample and/or test result.

One or more or all of the stored results may be obtained, preferably prior to the conduct of the method of analysing, by the analysis of an another test sample, for instance a sample from an unknown source. The another sample may be a sample from a known source, particularly a known person.

One or more of the stored results may be contributed to by a single source. One or more of the stored results may be contributed to by an unknown number of sources. One or more of the stored results may be contributed to by two or more sources. One or more of the two or more sources may be known, for instance the victim of the crime.

The analysis of the test sample may include one or more of: test sample preparation, purification, amplification, size based separation or electrophoresis. The analysis of the test sample may seek to establish the identity values present in respect of one or more identity variables at locations in the DNA of the test sample. The one or more identity variables may be the allele or alleles present at a locus. The analysis of the test sample may establish the one or more identity values present at one or more loci. The analysis of the test sample may establish the one or more identity values present at one or more loci in terms of an allele designation, for instance according to a recognised system of designation or according to size. The analysis of the test sample may establish the one or more identity values present at one or more loci in terms of a constrained range of possibilities, a constrained identity value.

The test result may be the output from the instrument performing the analysis of the test sample, particularly the physical analysis of the test sample.

The analysis, particularly the physical analysis, may be performed by an instrument which is separate from the apparatus providing one or more of the computer implemented steps and/or which is separate from the computer providing one or more of the computer implemented steps. The instrument providing the analysis, particularly the physical analysis, may be provided at a location remote from the location of the apparatus providing one or more of the computer implemented steps and/or from the location of the computer providing one or more of the computer implemented steps. The instrument and apparatus and/or computer may exchange data, for instance the test result, there between, particularly using a telecommunications network.

The processing of the test result may be provided according to the approach detailed in International Patent Publication number WO2009/066067 and/or US Patent Application Publication number US2009/0132173 and/or International Patent Publication number WO2010/116158.

The processing of the test result may include determining one or more or all of the possible identity value combinations which could have given rise to the test result data set. The processing of the test result may include determining one or more or all of the possible identity value combinations, expressed as allele values, which could have given rise to the test result data set.

The identity value may be expressed in terms of an allele designation, for instance according to a recognised system of designation or according to size. The identity value may be expressed in terms of a constrained range of possibilities, a constrained identity value, for instance in terms of two or more allele designations. The identity value or values may be present as an identity value combination.

The identity value or values may be the value for the identity variables considered in the analysis. One or more and preferably at least 8 loci may be considered in the analysis. The identity variables may be capable of heterozygous and/or homozygous variation. The variation may be one or more values selected from a limited number of values, for instance the known range of variation in the alleles for that locus.

The possible identity values may cover the variation possible, for instance one or more values selected from a limited number of values, for instance the known range of variation in the alleles for that locus. The possible identity values may include one or more numerical values. A numerical value may represent a single identity value for an identity variable, for instance an allele value for a locus. The possible identity values may include one or more non-numerical values, for instance a letter designation. A non-numerical value may represent two or more identity values for an identity variable, for instance two or more allele values for a locus. The constrained identity value may be a non-numerical value.

The constrained identity value may have a value equal to two or more of the possible identity values, for instance two or more allele values. The possible identity values may be those which exist or which are known for that identity variable, for instance that locus. The possible identity values may include the value "unknown" for the identity variable. The possible identity values may not be deemed to include the value "unknown" for the identity variable.

The test result data set may include one or more, preferably a plurality of, data sub-sets. A data sub-set may include one or more, preferably a plurality of, data elements. A data sub-set may include one or more, preferably a plurality of, data element types. One data element type may be a genotype and/or profile, particularly of an individual. A data sub-set may include two or more data elements of this type, preferably one for each individual contributing to the test sample under that explanation of the observed test result. One data element type may be a probability value. A data sub-set may include one data element of this type, particularly where the probability value relates to the probability of the combination of data elements of the genotype and/or profile form in that data sub-set. A data sub-set may include more than one data element of this type, particularly where the probability value relates to a single data element of the genotype and/or profile form in that data sub-set.

A data element of the genotype and/or profile form, preferably all such data elements, may be expressed in terms of the identity values and/or combination thereof. They may be expressed in terms of the identity values, with the identity values including and/or being associated with an indication of the locus those identity values are for.

The test result data set may include a plurality of data sub-sets each representing one or more possible genotypes and/or profiles, together with a probability value.

The test result data set may be processed to split the test result data set before the stored result data sets are processed to split the stored result data sets or the stored result data sets are processed to split the stored result data sets before the test result data set is processed to split the test result data set or the two splits may be processed at the same time or the two splits may be processed in sections.

The processing of the test results data set may include the selection of one or more test result data sets, potentially from a larger number of test result data sets.

The processing of the test results data set may include a first processor splitting the test results data set into a plurality of parts. The first processor may be a server. Each of the plurality of parts may be sent to a separate secondary processor. One or more or all of the secondary processors may be personal computers.

The splitting may split data which is specific to a locus from the data specific to one or more or all of the other loci. The splitting may split data which is specific to a part of a locus from the data specific another part of that locus and/or from data specific to one or more or all of the other loci. The splitting may split data relating to the identity values which are specific to a locus from the data relating to the identity values which are specific to one or more or all of the other loci. The splitting may split data relating to the identity values which are specific to a part of a locus from the data relating to the identity values which are specific another part of that locus and/or from data relating to the identity values which are specific to one or more or all of the other loci.

One or more or all of the plurality of parts may contain data specific to a locus. One or more or all of the plurality of parts may contain data specific to a part of a locus. One or more or all of the plurality of parts may contain data relating to the identity values which are specific to a locus. One or more or all of the plurality of parts may contain data relating to the identity values which are specific to a part of a locus.

One or more or all of the plurality of parts may contain a data set, including one or more data sub-sets and/or including one or more data elements, wherein the data is specific to a locus or a part of a locus. One or more or all of the plurality of parts may contain a data set, including one or more data sub-sets and/or including one or more data elements, wherein the information contained on the identity values and/or genotype and/or profile is specific to a locus or a part of a locus.

A secondary processor may be provided for each locus being analysed and/or being compared in the method. More than one secondary processor may be provided for one or more or all of the loci.

The method may include removing from and/or making a copy of, the probability information in a data set and/or data sub-set and/or data element. This may be done before the test result database is provided and/or before the processing of the test result data set to populate the test result database starts.

A test results database may be obtained for one or more or all of the plurality of parts.

One or more or all of the test result databases may be obtained using one or more or all of the following steps. An entry, for instance a slot, may be entered into the test results database for each different identity value combination and/or genotype and/or profile in the part. Preferably each different identity value combination and/or genotype and/or profile results in only one entry in the test results database. An identity value combination and/or genotype and/or profile may be taken from the part. The identity value combination and/or genotype and/or profile may be compared with the test results database content at that point in time. Preferably, if no entry corresponding to that identity value combination and/or genotype and/or profile is found, then a new entry is created. Preferably, if an entry corresponding to that identity value combination and/or genotype and/or profile is found, then no new entry is created. Preferably each combination and/or genotype and/or profile is compared with the test results database content until all the combinations and/or genotypes and/or profiles have been compared. Once all combinations and/or genotypes and/or profiles have been compared with the test results database content and the applicable entries made, the test results database may be deemed completed.

When an entry is made in the test results database, one or more pieces of information may be associated with the entry, directly or indirectly.

The one or more pieces of information may include an identifier, for instance a code number. The identifier may relate to the identity value combination and/or genotype and/or profile in a data set. The identifier may be specific to the data set. The identifier may relate to the identity value combination and/or genotype and/or profile in a data set sub-set. The identifier may be specific to the data sub-set. The identifier may be specific to a identity value combination and/or genotype and/or profile within the data set and/or within a dat sub-set. Preferably each identity value combination and/or genotype and/or profile within the data set and/or within a dat sub-set has its own identifier.

The one or more pieces of information may include an indication of which of the possible contributors to the test result and/or test result data set and/or data sub-set and/or data element, that piece of information and/or identifier relates to. Each identifier may be provided with such an indication.

The one or more pieces of information may include a further indication of the probability associated with the one or more pieces of information and/or identifier, for instance the probability of that identity value combination and/or genotype and/or profile and/or part thereof.

The obtaining of the stored results may be provided by accessing a plurality of records in a database. A record may contain a stored result.

The method may include the selection of one or more stored results. The selection may be from amongst a larger number of stored results. The stored results may number at least 100, preferably at least 1000, more preferably at least 10000 and ideally at least 1000000 such stored results. The stored results may be held in a database.

The storage of the stored results, particularly on a database, may be provided at a location which is separate from the apparatus providing one or more of the computer implemented steps and/or which is separate from the computer providing one or more of the computer implemented steps. The storage of the stored results, particularly on a database, may be provided at a location remote from the location of the apparatus providing one or more of the computer implemented steps and/or from the location of the computer providing one or more of the computer implemented steps. The storage location and/or database and the apparatus and/or the computer may exchange data, for instance the stored results, there between, particularly using a telecommunications network.

The processing of the stored results may include determining one or more or all of the possible identity value combinations which could have given rise to the stored result data sets. The processing of the stored results may include determining one or more or all of the possible identity value combinations, expressed as allele values, which could have given rise to the stored result data sets.

The identity value may be expressed in terms of an allele designation, for instance according to a recognised system of designation or according to size. The identity value may be expressed in terms of a constrained range of possibilities, a constrained identity value, for instance in terms of two or more allele designations. The identity value or values may be present as an identity value combination.

The identity value or values may be the value for the identity variables considered in the analysis. One or more and preferably at least 8 loci may be considered in the analysis. The identity variables may be capable of heterozygous and/or homozygous variation. The variation may be one or more values selected from a limited number of values, for instance the known range of variation in the alleles for that locus.

The possible identity values may cover the variation possible, for instance one or more values selected from a limited number of values, for instance the known range of variation in the alleles for that locus. The possible identity values may include one or more numerical values. A numerical value may represent a single identity value for an identity variable, for instance an allele value for a locus. The possible identity values may include one or more non-numerical values, for instance a letter designation. A non-numerical value may represent two or more identity values for an identity variable, for instance two or more allele values for a locus. The constrained identity value may be a non-numerical value.

The constrained identity value may have a value equal to two or more of the possible identity values, for instance two or more allele values. The possible identity values may be those which exist or which are known for that identity variable, for instance that locus. The possible identity values may include the value "unknown" for the identity variable. The possible identity values may not be deemed to include the value "unknown" for the identity variable.

The stored result data sets may include one or more, preferably a plurality of data sub-sets. A data sub-set may include one or more, preferably a plurality of, data elements. A data sub-set may include one or more, preferably a plurality of, data element types. One data element type may be a genotype and/or profile, particularly of an individual. A data sub-set may include two or more data elements of this type, preferably one for each individual contributing to the test sample under that explanation of the observed test result. One data element type may be a probability value. A data sub-set may include one data element of this type, particularly where the probability value relates to the probability of the combination of data elements of the genotype and/or profile form in that data sub-set. A data sub-set may include more than one data element of this type, particularly where the probability value relates to a single data element of the genotype and/or profile form in that data sub-set.

A data element of the genotype and/or profile form, preferably all such data elements, may be expressed in terms of the identity values and/or combination thereof. They may be expressed in terms of the identity values, with the identity values including and/or being associated with an indication of the locus those identity values are for.

The stored result data sets may include a plurality of data sub-sets each representing one or more possible genotypes and/or profiles, together with a probability value.

The processing of the stored result data sets may include the selection of one or more stored result data sets, potentially from a larger number of stored result data sets.

The processing of the stored results data sets may include a first processor splitting the stored results data sets into a plurality of parts. The first processor may be a server. Each of the plurality of parts may be sent to a separate secondary processor. One or more or all of the secondary processors may be personal computers.

The first processor and/or the second processors are preferably the first processor and/or the second processors used to process the test result data set.

The splitting may split data which is specific to a locus from the data specific to one or more or all of the other loci. The splitting may split data which is specific to a part of a locus from the data specific another part of that locus and/or from data specific to one or more or all of the other loci. The splitting may split data relating to the identity values which are specific to a locus from the data relating to the identity values which are specific to one or more or all of the other loci. The splitting may split data relating to the identity values which are specific to a part of a locus from the data relating to the identity values which are specific another part of that locus and/or from data relating to the identity values which are specific to one or more or all of the other loci.

One or more or all of the plurality of parts may contain data specific to a locus. One or more or all of the plurality of parts may contain data specific to a part of a locus. One or more or all of the plurality of parts may contain data relating to the identity values which are specific to a locus. One or more or all of the plurality of parts may contain data relating to the identity values which are specific to a part of a locus.

One or more or all of the plurality of parts may contain a data set, including one or more data sub-sets and/or including one or more data elements, wherein the data is specific to a locus or a part of a locus. One or more or all of the plurality of parts may contain a data set, including one or more data sub-sets and/or including one or more data elements, wherein the information contained on the identity values and/or genotype and/or profile is specific to a locus or a part of a locus.

A secondary processor may be provided for each locus being analysed and/or being compared in the method. More than one secondary processor may be provided for one or more or all of the loci.

The method may include removing from and/or making a copy of, the probability information in a data set and/or data sub-set and/or data element. This may be done before the stored result database is provided and/or before the processing of the stored result data sets to populate the stored result database starts.

A stored results database may be obtained for one or more or all of the plurality of parts.

One or more or all of the stored result databases may be obtained using one or more or all of the following steps. An entry, for instance a slot, may be entered into the stored results database for each different identity value combination and/or genotype and/or profile in the part. Preferably each different identity value combination and/or genotype and/or profile results in only one entry in the stored results database. An identity value combination and/or genotype and/or profile may be taken from the part. The identity value combination and/or genotype and/or profile may be compared with the stored results database content at that point in time. Preferably, if no entry corresponding to that identity value combination and/or genotype and/or profile is found, then a new entry is created. Preferably, if an entry corresponding to that identity value combination and/or genotype and/or profile is found, then no new entry is created. Preferably each combination and/or genotype and/or profile is compared with the stored results database content until all the combinations and/or genotypes and/or profiles have been compared. Once all combinations and/or genotypes and/or profiles have been compared with the stored results database content and the applicable entries made, the stored results database may be deemed completed.

When an entry is made in the stored results database, one or more pieces of information may be associated with the entry, directly or indirectly.

The one or more pieces of information may include an identifier, for instance a code number. The identifier may relate to the identity value combination and/or genotype and/or profile in a data set. The identifier may be specific to the data set. The identifier may relate to the identity value combination and/or genotype and/or profile in a data set sub-set. The identifier may be specific to the data sub-set. The identifier may be specific to a identity value combination and/or genotype and/or profile within the data set and/or within a dat sub-set. Preferably each identity value combination and/or genotype and/or profile within the data set and/or within a dat sub-set has its own identifier.

The one or more pieces of information may include an indication of which of the possible contributors to the test result and/or test result data set and/or data sub-set and/or data element, that piece of information and/or identifier relates to. Each identifier may be provided with such an indication.

The one or more pieces of information may include a further indication of the probability associated with the one or more pieces of information and/or identifier, for instance the probability of that identity value combination and/or genotype and/or profile and/or part thereof.

The identity values and/or identity value combinations and/or genotypes and/or profiles and/or data set and/or data sub-set and/or data elements and/or results database and/or one or more pieces of information and/or identifier and/or further indication may be in the same format for the test results and/or test results data set as for the stored results and/or stored results data sets.

The method may include the provision of a user interface, such as a keyboard, and/or a user display, such as a screen, and/or a data storage device.

Preferably at least one test result database is formed for each locus being considered. Preferably at least one stored results database is formed for each locus being considered. Preferably the same number of test result databases and stored results database are provided. Preferably test result databases and stored results database are provided for the same loci or parts thereof.

Preferably the first test results database and the first stored results database are provided on the same, preferably second, processor. Preferably each test results database and each stored results database are provided on the same, preferably second, processor as one another.

The method may include comparing the first test result database with the first stored result database using one or more or all of the following steps. An entry, for instance a slot, in the first test results database may be selected. The entry may be compared with the first stored results database content. Preferably, if an entry corresponding to that entry is found, then a note is made in a first match list. Preferably, if no entry corresponding to that entry is found, then no note is made in the first match list. Preferably each entry in the first test result database is compared with the stored results database content until all the entries in the first test result database have been compared. Once all the entries in the first test results database have been compared with the stored results database content and the applicable notes made, the step may be deemed completed. The process could be performed the other way around, with an entry from the first stored results database being taken and compared with the first test result database.

The method may include comparing the test result database with the stored result database for each pair of test result database and stored result database, using one or more or all of the following steps. An entry, for instance a slot, in the second and/or other test results databases may be selected. The entry may be compared with the second and/or other stored results database content. Preferably, if an entry corresponding to that entry is found, then a note is made in a second and/or other match list. Preferably, if no entry corresponding to that entry is found, then no note is made in the second and/or other match list. Preferably each entry in the second and/or other test result database is compared with the stored results database content until all the entries in the second and/or other test result database have been compared. Once all the entries in the second and/or other test results database have been compared with the stored results database content and the applicable notes made, the step may be deemed completed. The process could be performed the other way around, with an entry from the second and/or other stored results database being taken and compared with the second and/or other test result database.

The method may include the length and/or size and/or number of notes in a match list being communicated, preferably from the secondary processor where the match list was created to a first processor. A copy of the match list may be provided to the first processor.

The method may include a first processor instructing a second processor to provide a copy of its match list to another second processor. The second processor may be the processor with the shortest and/or smallest and/or fewest number of notes match list reported to the first processor at that time. The another second processor may be the second processor with the longest and/or largest and/or greatest number of notes match list reported to the first processor at that time.

The method may include comparing the first match list with the second match list using one or more of the following steps. A note in one of the match lists, preferably the shorter and/or smallest and/or fewest number of notes match list may be selected. The note may be compared with the other of the match lists, particularly the one on that processor. Preferably, if a note corresponding to that note is found, then a further note is made in first further match list. Preferably, if no note corresponding to that note is found, then no note is made in the first further match list. Preferably each note on the match list is compared with the other match list content until all the notes in the match list have been compared with the other match list. Once all the notes in the match list have been compared with the other match list and the applicable further notes made, the step may be deemed completed.

The method may include comparing an other match list, for instance a third match list, being compared with a further other match list, such as a fourth match list, using one or more of the following steps. A note in one of the match lists, preferably the shorter and/or smallest and/or fewest number of notes match list may be selected. The note may be compared with the other of the match lists, particularly the one on that processor. Preferably, if a note corresponding to that note is found, then a further note is made in an another further match list, such as a second further match list. Preferably, if no note corresponding to that note is found, then no note is made in the another further match list, such as a second further match list. Preferably each note on the match list is compared with the other match list content until all the notes in the match list have been compared with the other match list. Once all the notes in the match list have been compared with the other match list and the applicable further notes made, the step may be deemed completed.

The method may include the length and/or size and/or number of notes in the first further match list being communicated, preferably from the secondary processor where the match list was created to a first processor. A copy of the further match list may be provided to the first processor.

The method may include a first processor instructing a second processor to provide a copy of its further match list to another second processor. The second processor may be the processor with the shortest and/or smallest and/or fewest number of notes in the further match list reported to the first processor at that time. The another second processor may be the second processor with the longest and/or largest and/or greatest number of notes in the further match list reported to the first processor at that time.

The first further match list may include a note for each entry present in both pairs of databases.

The method may provide for the comparison of the further match lists, preferably in the same manner as detailed in the proceeding paragraphs for the match lists, to generate a filtered match list. Each filter match list may be obtained by comparing the results of two pairs of comparisons. In the comparison a further match list may be compared with another of the further match lists and/or with another of the match lists.

The filtered match list may include a note for each entry present in all four pairs of databases.

The method may provide for the comparison of the filtered match lists, preferably in the same manner as detailed in the proceeding paragraphs for the match lists, to generate a further filtered match list. Each further filter match list may be obtained by comparing the results of four pairs of comparisons.

The further filtered match list may include a note for each entry present in all eight pairs of databases.

The method may provide for repeats of the comparisons until all of the databases have been compared and, preferably, a final match list is reached.

The final match list may include a note for each entry present in all of the pairs of databases.

One or more of the comparisons may commence before one or more of the other comparisons have finished.

The note in the match lists may be the identifier, for instance the code.

The final match list may represent a list of those stored samples which are a potential match for the test sample across all of the loci analysed and/or compared. The final match list may represent a list of the genotypes and/or profiles within a stored sample which are a potential match for the genotype and/or profile within the test sample across all loci analysed and/or compared.

The notes in the final match list may be combined with the probability information for them. The probability information may provide a probability of a match for one or more or all of those stored samples which are a potential match for the test sample across all of the loci analysed and/or compared. The probability information may provide a probability of a match for one or more or all of genotypes and/or profiles within a stored sample which are a potential match for the genotype and/or profile within the test sample across all loci analysed and/or compared.

The probability information may be used to provide a ranked list for the notes which are deemed a match across all the loci compared and/or analysed.

The allocating of a probability and/or a probabilistic weighting may be made based upon a value associated with a test result. The value may be associates with the test result during the processing of the test sample analysis data set to the test sample results data set. The value may be associated with the test result according to the approach detailed in International Patent Publication number WOWO2009/066067 and/or US Patent Application Publication number US2009/0132173 and/or International Patent Publication number WO2010/116158.

The probability and/or probabilistic weighting allocated for one identity variable may be combined with the probability and/or probabilistic weighting allocated to one or more or all the other identity variables. They may be combined by addition or multiplication.

The ranking be from highest value to lowest value. The ranking may be from the lowest value to the highest value. Those rankings above a threshold value may be excluded and/or included in a further consideration. Those rankings below a threshold value may be excluded and/or included in a further consideration.

The combined value may be used in the ranking.

The further consideration may be in legal proceedings as evidence and/or in determining an action to take in an investigation by a law enforcement authority.

The method may be applied to test result data sets and/or stored results data sets with respect to a plurality of different identity variables, for instance a plurality of different loci.

The identity values for one or more of the identity variables considered in the analysis may be obtained for a plurality of identity variables, preferably 5 or more, ideally with the identity variables being different loci.

The comparing may be used to considered evidence, for instance in civil or criminal legal proceedings. The comparing may make a comparison as to the relative likelihoods, for instance a likelihood ratio, of one hypothesis to another hypothesis. The comparing may make a comparison as to the relative likelihoods of the evidence relating to one hypothesis to another hypothesis. In particular, this may be a hypothesis advanced by the prosecution in the legal proceedings and another hypothesis advanced by the defence in the legal proceedings. The likelihood ratio may be of the form:

$$LR = \frac{p(c, gs \mid V_p)}{p(c, gs \mid V_d)} = \frac{f(c \mid gs, V_p)}{f\ c \mid gs, V_d)}$$

where
1. c is the test result data set from a test sample, more particularly, the test result data set taken from a sample recovered from a person or location linked with a crime, potentially expressed in terms of peak positions and/or heights and/or areas;
2. gs is the stored result data set, more particularly, the stored result data set taken from a sample collected from a person, particularly expressed as a suspect's genotype;
3. $V_p$ is one hypothesis, more particularly the prosecution hypothesis in legal proceedings stating "The suspect left the sample at the scene of crime";
4. $V_d$ is an alternative hypothesis, more particularly the defence hypothesis in legal proceedings stating "Someone else left the sample at the crime scene".

The comparing may provide for a step including or providing a Likelihood Ratio, LR. The LR may summarise the value of the evidence in providing support to a pair of competing propositions: one of them representing the view of the prosecution ($V_p$) and the other the view of the defence ($V_d$). The propositions may be:
 1) $V_p$: The suspect is the donor of the DNA in the test sample;
 2) $V_d$: Someone else is the donor of the DNA in the test sample.

The method of comparing may be used to gather information to assist further investigations or legal proceedings. The method of comparing may provide intelligence on a situation. The method of comparing may be of the likelihood of the information of the test sample result given the information of the another sample result. The method of comparing may provide a listing of possible another sample results, ideally ranked according to the likelihood. The method of comparing may seek to establish a link between a DNA profile from a crime scene sample, a test sample, and one or more DNA profiles stored in a database, an another sample.

The method of comparing may provide a link between a DNA profile, for instance from a crime scene sample, and one or more profiles, for instance one or more profiles stored in a database.

The method of comparing may consider a crime profile with the crime profile consisting of a set of crime profiles, where each member of the set is the crime profile of a particular locus. The method may propose, for instance as a process outcome, a list of profiles from the database. The method may propose a posterior probability for one or more or each of the profiles. The method may propose, for instance as a process outcome, a list of profiles, for instance ranked such that the first profile in the list is the genotype of the most likely donor.

The method may further provide that where one or more potential matches are identified, a decision may be taken. The decision may be to take one or more actions. The method may include performing one or more actions. The method may include a step for deciding to perform one or more actions and/or for instructing the performance of one or more action and/or for performing one or more actions.

The method may further provide that where no potential matches are identified, a decision may be taken and/or an instruction may be given. The decision and/or instruction may be different to the decision taken where one or more potential matches are identified. The decision and/or instruction may be to take one or more actions. The one or more actions may be different to the one or more actions taken where one or more potential matches are identified. The decision and/or instruction may be not to take one or more actions. The method may include a step for performing one or more actions The method may include a step for performing one or more actions where one or more potential matches are identified.

The method may include a step for performing one or more actions where no potential matches are identified.

The method may include a step for collecting a subsequent sample, such as a subsequent test sample.

The method may include a step for performing an analysis of a subsequent sample, such as on the subsequent test sample.

The subsequent sample may be a subsequent sample taken from the test sample and/or a subsequent sample taken from the same source as the test sample. The subsequent sample may be another part or aliquot of the test sample. The subsequent sample may be a new subsequent sample taken from the same source as the test sample. The source may be an item and/or a location and/or a person.

The subsequent sample may be a subsequent sample taken from the another sample and/or a subsequent sample taken from the same source as the another sample and/or stored result. The subsequent sample may be another part or aliquot of the another sample. The subsequent sample may be a new subsequent sample taken from the same source as the another sample. The source may be an item and/or a location and/or a person.

The subsequent sample may be collected from an item and/or a location and/or a person.

The subsequent sample may be analysed by a physical analysis method. The physical analysis method may include one or more of test sample preparation, purification, amplification, size based separation, electrophoresis, fluorescence or light detection. The analysis method may seek to establish the identity values for present in respect of one or more identity variables st locations in the DNA of the subsequent sample. The one or more identity variables may be the allele or alleles present at a locus. The analysis may establish the one or more identity values present at one or more loci. The analysis may establish the one or more identity values present at one or more loci in terms of allele designation, for instance according to a recognised system of designation according to size. The analysis may establish the one or more identity values present at one or more loci in terms of a constrained range of possibilities, a constrained identity value.

The subsequent sample may be processed using one or more steps of the aspects of the invention and/or according to the aspects of the invention and/or according to any of the options or possibilities set out elsewhere within this application. The subsequent sample may be compared with the another sample and/or with a different another sample and/or with a different subsequent sample and/or with a stored result and/or with a different stored result and/or a subsequent stored result.

The method may include a step for moving an item from a first state to a second state. The first state may be a position. The second state may be a position. Preferably the first state is a first position and the second state is a second different position.

The item may be the source of a subsequent sample. The item may be a sample collection container, sample collection device or sample. The item may be a vehicle. The item may be a person. The person may be the source of a sample and/or test sample and/or another sample and/or subsequent sample.

Any of the proceeding aspects of the invention may include the following features, options or possibilities or those set out elsewhere in this document.

Various embodiments of the invention will now be described, by way of example only and with reference to the accompanying drawings in which.

CONTEXT AND BACKGROUND TO THE INVENTION

Figure 1:
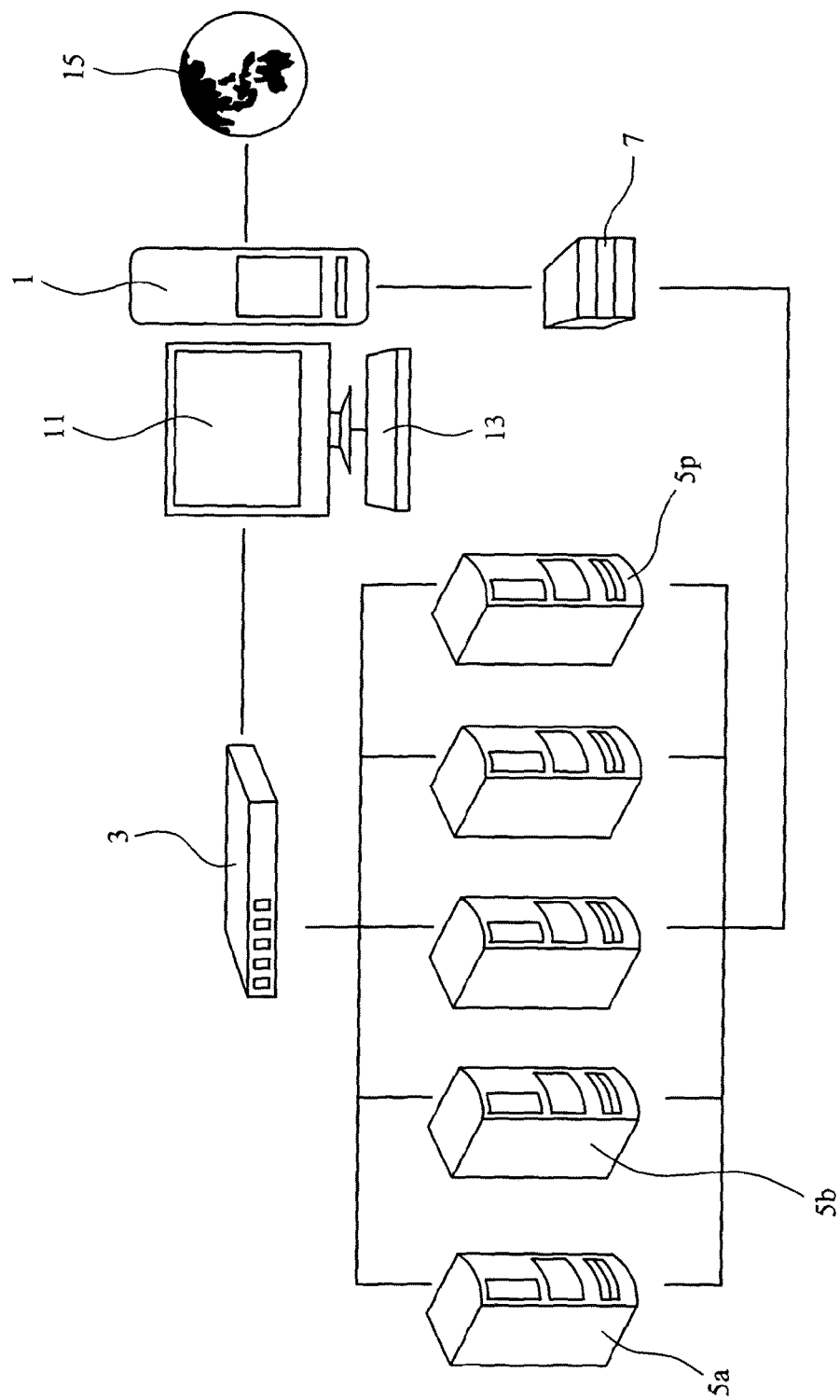
FIG. 1 is a schematic illustration of a hardware configuration suitable for providing an embodiment of the present invention.
Figure 2:
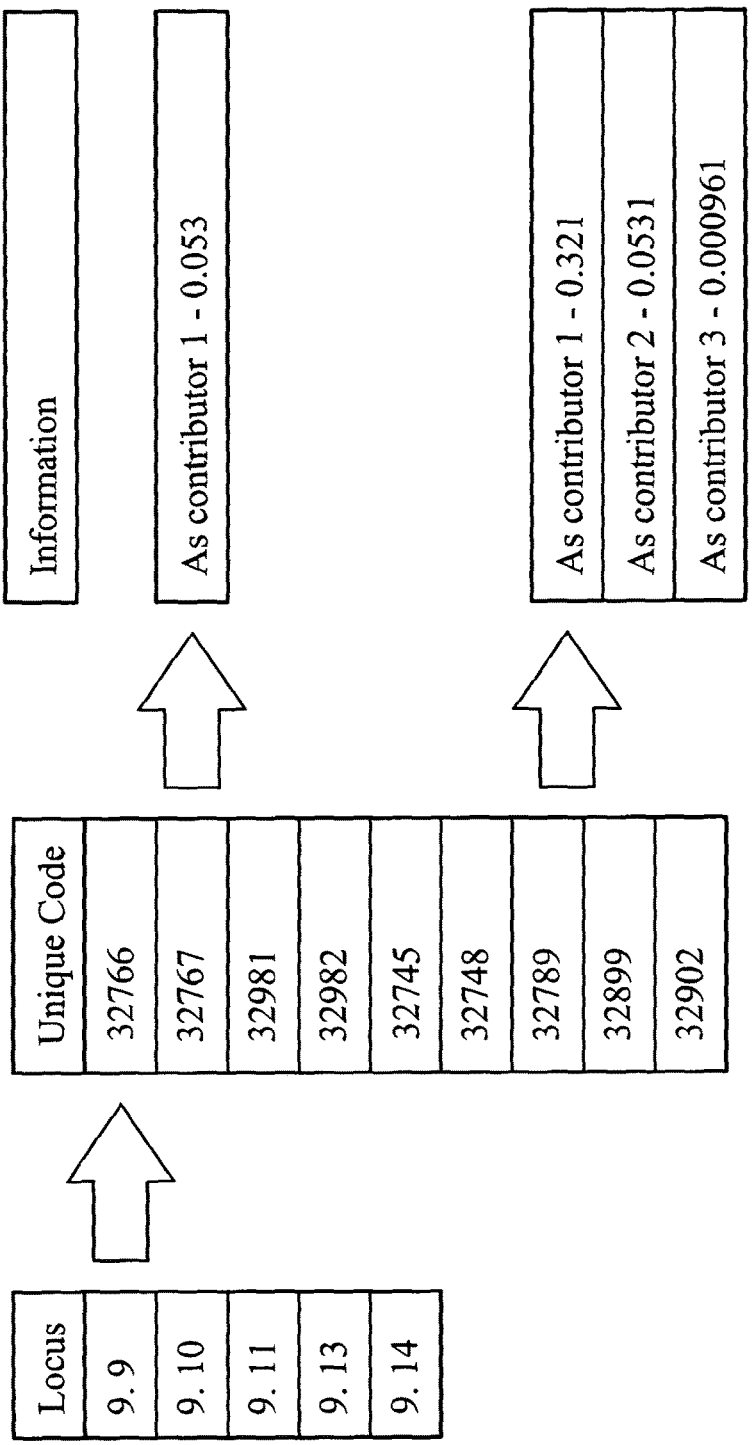
FIG. 2 is an example of some locus specific slots and the unique codes and other information associated with them.

The present invention is concerned with improving the interpretation of results from DNA analysis. In particular, the invention improves the manner in which a test result from a test sample is considered against a plurality of stored test results. The number of stored test results used in the consideration can be vast. The consideration is often intended to give an outcome, for instance, the presence of one or more matches and/or a likelihood of that match. Basically, the DNA analysis involves taking a sample of DNA and analysing the variations present at a number of loci. The identities of the variations give rise to a data set which is then interpreted to give a profile or genotype. This may form the test result. Once the process has been completed for a test result, the test result is often then one of the stored results in the context of a subsequent consideration. The extent of interpretation required can be extensive and/or introduce uncertainties. This is particularly so where the DNA sample contains DNA from more than one person, a mixture.

There is often a need to consider various hypotheses for the identities of the persons responsible for the DNA and evaluate the likelihood of those hypotheses; evidential uses.

There is often a need to consider the analysis profile or genotype, test result, against a database of profiles or genotypes, stored results, so as to establish a list of stored profiles or genotypes that are likely matches with the analysis profile or genotype; intelligence uses.

In support of this analysis, the applicant has developed and disclosed a mathematical specification of a model for computing likelihood ratios (LRs) that uses peak heights taken from such DNA analysis. The approach draws on an estimation of a two-dimensional, 2D, probability density function, pdf, which is estimated from the heights or areas of peaks observed after the analysis of control samples. Such pdf's may be generated from heterozygous donors and separately from homozygous donors. The approach goes on to calculate the probability of dropout and achieve other benefits. Full details of these developments are to be found in International Patent Publication number WOWO2009/066067 and/or US Patent Application Publication number US2009/0132173, the contents of both of which are fully incorporated herein by reference, particularly with respect to the analysis of the samples, their mathematical expression and their comparison with others, including the determination of the likelihood ratio for a match between them.

Subsequently, the applicant has developed that technology further. The statistical model now provides for computing likelihood ratios for single profiles and mixed profiles while considering peak heights or areas, but also takes into consideration allelic dropout and stutters. In this way, the technique makes far greater use of a far greater proportion of the information in the results and hence give a more informative and useful overall result.

To achieve this, the present invention includes the use of a number of components. The main components of the approach are:

1. An estimated PDF for homozygote peaks conditional on DNA quantity;
2. An estimated PDF for stutter heights conditional on the height of the parent allele;
3. An estimated joint probability density function (PDF) of peak height pairs conditional on DNA quantity;
4. A latent variable X representing DNA quantity that models the variability of peak heights across the profile.
5. The calculation of the LR is done separately for the numerator and the denominator. The overall joint PDF for the numerator and the denominator can be represented with Bayesian networks (BNs).

Full details of these further developments to the technology are included in International. Patent Publication number WO2010/116158, the contents of which are fully incorporated herein by reference, particularly with respect to the analysis of the samples, generation of the test results and/or stored results, their mathematical expression and their comparison with others, including the determination of the likelihood ratio for a match between them.

The use of such technology, and potentially other approaches, for the consideration of the DNA sample gives a test result, and hence stored results, which include a data set. This data set includes a far larger volume of data in the data set than was produced under previous approaches. This is beneficial in terms of the information which may be obtained and the ability to consider a wider range of possible matches. The volume of data in the data set may be larger because instead of reaching a single or relatively limited number of possibilities (expressed as possible alleles/identities at one or more loci, through to expression as a profiles or genotypes through interpretation of the results), the results include a far larger number of possibilities (expressed as possible alleles/identities at one or more loci, through to expression as a profiles or genotypes). In general, a test result provides a data set which is fainted of a series of sub-sets. Each sub-set is formed of data elements, with a data element for the genotype and/or profile of each person deemed to have contributed to the sample and an expression of the probability of that combination of genotypes and/or profiles. Thus a sample which was a mixture of two people's DNA could have a sub-set formed of a first genotype, a second genotype and an expression of the probability of that combination of two genotypes. This format for the data set will also be present, therefore, when the test result becomes one of the many stored results. In general, the data set is in the form of a vector made up, potentially by a large number, of the sub-sets.

However, the number of combinations in a data set represented by the sub-sets and/or the format of the data sets also creates problems with respect to the computation resources and/or time needed to process the subsequent data processing stages. A much larger number of possibilities needs to be considered against others to see if there is a match.

Overview of the Invention—Hardware Configuration

In prior art approaches to considering the test result against stored results to consider whether there is a match and/or give a likelihood of a match, the entirety of the data set forming the test result is considered against the entirety of the data set forming the stored results with respect to all of the stored results. This means the test result is compared with a vast number of stored results in large databases, such as The National DNA Database® operated in the UK.

The type of developments identified about greatly increase the amount of data which forms the data set for the test result and the stored results, hence greatly increasing the computational needs for making such a comparison. The present invention seeks to avoid this problem by materially reducing the computational need. This is achieved through a different hardware structure and through a different organisation of the comparison of the data set for the test sample with the data set for the stored samples.

FIG. 1 shows a schematic of a hardware configuration suitable for use in the present invention. A master node 1 is provided which is connected to a switching unit 3 to allow communications between the master node 1 and one or more of a set of worker nodes 5. In this case, sixteen separate worker nodes, 5a, 5b, . . . 5p, are provided. Each of the worker nodes 5 are connected to each other. Each of the worker nodes 5 are connected to a data storage device 7. The data storage device 7 is also connected to the master node 1. In this specific example, the master node 1 is in the form of a server 9 and accompanying user display 11 and interface 13. The switching unit 3 is an Ethernet switch, such as a 10/100 Mbs Ethernet switch. The worker nodes 5 are each provided by a unit of the same type and specification (speed, RAM, ROM etc) and can be personal computer type units.

The system, potentially via the master node 1 is provide with an optional connection to the Internet 15. This can be used to provide communications between the system and other locations. The other location may be those at which further results are generated by the collection, analysis and reporting of results. Connection to other communications networks, internal to the operating organisation and/or external thereto, can be provided.

A computer cluster of this type is capable of achieving high rates of computation by linking the master node 1 and worker nodes 5 so that they work closely together. Such a cluster is capable of performing parallel computing, where multiple calculations are performed concurrently. Such clusters may use the Linix operating systems, open source software and a TCP/IP LAN as the network.

In operation, the master node 1 is responsible for allocating the work to the worker nodes 5.

The use of a cluster of this type offers improved computing performance which is beneficial in the context of the computations the present invention is concerned with.

Further Benefits and Details of the Hardware Approach

As mentioned above, the use of a cluster of this type offers improved computing performance which is beneficial in the context of the computations the present invention is concerned with. This comes in a number of ways.

Firstly, a parallel processing cluster is capable of high computational rates.

Secondly, such a configuration of the hardware is highly scalable. In the example described above, sixteen worker nodes are used so that each of the loci considered by the multiplex of primers, which is used to amplify parts of the DNA sample, are handled on a different worker node 5 from the other loci. If the system needed to switch to a larger multiplex, for instance a thirty two plex, to give greater discrimination power, it is a simple task to increase the number of worker nodes 5 in the system. A worker node 5 for each loci can be provided still and a similar level of performance can be obtained. In other instances, the computational load may prove too great with respect to one or more of the sixteen loci being considered. In such a case, it is possible to split one or more of the loci so that the single loci is handled on two different worker nodes 5. Hence, scaling up of the number of worker nodes provided can be used to maintain computational performance.

Overview of the Invention—Processes Applied

Generally, the process involves a number of different stages/sub-stages:
  a) A stored result selection and plurality of stored result database creation stage;
  b) A test result against stored result comparison stage, including:
    1) A test result selection and plurality of test result database creation sub-stage;
    2) A single test result database against single stored result database search sub-stage, performed for the various pairs of test result databases and stored result databases, to establish matches;
    3) An established match review sub-stage, to filter out established matches which do not feature as matches across the other test result against stored result databases;
    4) A process outcome sub-stage which provides details of the matches which extend across all the database pairs.

In the present invention, further benefits are obtained through the manner in which these stages and/or sub-stages are assigned to and/or performed by the master node 1 and worker nodes 5 used in the process to provide the consideration/comparison between the test sample and the stored samples.

An explanation and further details for each of these stages and sub-stages are provided in the sections set out below.

A variety of possibilities exist for deploying such an approach in terms of the code used. However, the following pseudo code provides a useful indication of the general requirements involved:

[Pseudo Code]

Master Node receives collection of samples
While (there are still samples to be searched)
    Send locus information to appropriate worker-nodes
    Worker-node creates search-term
    Search-term is run against database
    Unique identifiers list returned to master-node
    Master-node coordinates synchronisation of lists from each worker-node
    Synchronised list sent to each worker-node
    Worker-node returns results for each unique identifier in synchronised list
    Combine results from each worker-node into a collection

```
    Return collection
Endwhile
```

Further Benefits and Details of the Stored Result Selection and Plurality of Stored Result Database Creation Stage As mentioned above, the invention differs in the manner in which the test result and the stored results are considered. In particular, there is a comparison of less than the entirety of the data set for a test result with less than the entirety of the data set for each stored result. In particular, certain elements from within the sub-sets of the data are considered separately from others.

As a first stage, the system must be prepared with respect to the stored results against which a comparison with a test result is to occur.

As an initial step, a selection is made of those stored results to be considered. This may be a selection from a larger number of stored results which are available or may be all of the stored results.

For those selected stored results, they are provided to the master node 1. This may be from a data storage device 7 within the system or form outside, for instance using the connection to the Internet. The stored results include a data set in each case. As mentioned above, the data set includes a series of sub-sets. Each sub-set is formed of data elements, with a data element for the genotype and/or profile of each person deemed to have contributed to the sample and an expression of the probability of that combination of genotypes and/or profiles. The data element for the genotype and/or profile will reflect, in terms of the data sub-elements present, the allele identities for each of the different loci in respect of which results were collected in the physical analysis stage.

Having received the stored results, the master node 1 processes those to divide out the data to be provided to each of the worker nodes 5 for the subsequent processing. The intention is to provide each worker node only with the information it needs. In this preferred embodiment, that involves sending a worker node only the data sub-elements which relate to the locus it is concerned with processing. Thus the data for locus vWA may be provided to worker node 5a, the data for locus D21S11 to worker node 5b and so on. The worker node data set includes for a stored result, sub-elements relating to the identities observed in the analysis for that locus for each of the genotypes and/or profiles in a combination represented by a sub-set, together with the probability information for that combination. This is repeated for each of the combinations in each of the stored results.

Having sent the data from the master node to the worker nodes, the focus of the processing moves to the worker nodes. Each worker node acts in an equivalent manner on the locus specific data it has received.

The worker node is required to establish a database which represents all of the identity combinations observed in at least one of the genotypes and/or profiles in at least one of the combinations in at least one of the stored results. This can be thought of as the creation of the locus-estate for the stored results.

In doing so, the worker node applies the same process to each of the sub-sets. First, the worker node stores the probability for that combination for later use. The worker node then looks to see whether the identity information for one of the genotypes and/or profiles in that combination corresponds to an entry in the database being created. If not, then an entry in the database is generated for that identity information. The next genotype and/or profile in that combination is then considered. If there is no corresponding entry, then one is created. If there is a corresponding entry already, then no new entry is needed. Once all of the genotypes and/or profiles in a combination are considered in this way, the worker node advances to the next combination and works through the genotypes and/or profiles therein. Once all of the stored results have been processed in this way, the stored result database is completed. There is an entry or slot, but only one, for each identity information form observed in all of the combinations in all of the stored results.

For each entry or slot, the database has further associated information. This is best understood in the context of the example of FIG. 3 and the text below.

In the example, five of the slots established for that locus are shown (left column). These are designated by the allele designations attributed to the identities observed for that slot. Thus, the top slot is homozygous with respect to alleles 9, 9; the next slot is heterozygous with respect to alleles 9, 10; and so on. Each slot has linked to it, a collection of profiles and/or genotypes (eight in the example) which had the identities of that slot. For each of these profiles, a unique coding is present (middle column). In this case, a five digit number is used, but there are many possibilities. This unique code forms a link between the slot and the origins of the profile. Also present (right column) is information for each of the profiles and/or genotypes, as to which of the contributors within that result gave rise to the profile and/or genotype, together with the probability information (expressed here as a number between 0 and 1).

This process can be thought of in terms of the following Pseudo code for its implementation by the master node:
[Pseudo Code]

```
master-node receives sample
For each (locus in sample)
    Send locus information to appropriate worker-node
EndFor
While (there are any worker-nodes still to finish)
    For each (worker-node that has not finished)
        Check if worker-node has finished creating locus-estate
        If (worker-node has finished)
            Mark worker-node as finished
        EndIf
    EndFor
Endwhile
``` and the process can be thought of in terms of the following Pseudo code for its implementation by the worker-nodes:
[Pseudo Code]

```
Worker-node receives locus information from master-node
E2-vector information is extracted from the locus information
For each (combination in the E2 vector)
    If (combination is included for searching)
        For each (potential contributor)
            Extract genotype from combination
            If (genotype not already present in the locus-estate)
                Create a new genotype-slot to store that genotype and place in the locus-estate
            EndIf
            Get genotype-slot and store E2 vector information in it
        EndFor
    EndIf
EndFor
``` where the E2 vector information is the probability information discussed elsewhere.

The above processing can be performed by each worker node 5 in parallel and can start as soon as data is transferred to the worker node for the first of the stored results. This speeds up the implementation. Furthermore, the compilation of the database is made through a relatively easy and low computational demand process by virtue of the checking of the identity information against, in effect, a list of those already seen in previous stored results which have been processed.

Having completed this stage, the process can advance to the test result against stored result comparison stage, and in particular the test result selection and plurality of test result database creation sub-stage.

Further Benefits and Details of the Test Result Selection and Plurality of Test Result Database Creation Sub-Stage As an initial step, a selection is made of the test result to be considered. This may be a selection from a larger number of test results and could be more than one test result for processing in parallel.

The selected test results is provided to the master node 1. This may be from a data storage device 7 within the system or form outside, for instance using the connection to the Internet. Just as with the stored results, the test result includes a data set and the data set has the same format.

Having received the test result, the master node 1 processes it to divide out the data to be provided to each of the worker nodes 5 for the subsequent processing; just as with the stored results. The worker node data set includes for a test result, sub-elements relating to the identities observed in the analysis for that locus for each of the genotypes and/or profiles in a combination represented by a sub-set, together with the probability information for that combination.

Each worker node acts in an equivalent manner on the locus specific data it has received.

The worker node is required to establish a test result database which represents all of the identity combinations observed in at least one of the genotypes and/or profiles in at least one of the combinations in the test result. This can be thought of as the creation of the locus-estate for the test result.

In doing so, the worker node applies the same process to each of the sub-sets. First, the worker node stores the probability for that combination for later use. The worker node then looks to see whether the identity information for one of the genotypes and/or profiles in that combination corresponds to an entry in the database being created. If not, then an entry in the database is generated for that identity information. The next genotype and/or profile in that combination is then considered. If there is no corresponding entry, then one is created. If there is a corresponding entry already, then no new entry is needed. Once all of the genotypes and/or profiles in the combination which represents the test result are considered in this way, the sub-stage is complete. There is an entry or slot, but only one, for each identity information form observed in all of the combinations in the test result.

The same information as to the unique code, contributor and probability as was described above for the stored results, is obtained for the test results.

The next sub-stage can then be performed.

Further Benefits and Details of the Single Test Result Database Against Single Stored Result Database Search Sub-Stage With all the stored samples loaded and the stored result database created for each locus and with the test result loaded and the test result database created for each locus, it is possible to start the comparison.

The comparison is only carried out on worker nodes and is performed in an equivalent manner on each, in parallel.

As described above, the test result database for a locus has an entry or slot for each of the identity information form observed in it. The comparison takes a slot from the test result database, and looks to see whether there is a match for this test result slot in the slots of the stored result database.

When a match is observed, then a note is made in a match list. The note means that slot is included in those for which a match is established at that locus. The note provides a link to not just the slot, but also to the unique codes behind that slot (as described above in the example) and the information behind that, as to contributor and probability.

When a match is not observed, then no note is added to the match list.

This process is repeated until all of the test result slots have been considered against the slots in the stored sample database for that locus. The process is taken to completion on each of the locus specific worker nodes 5.

This process can be thought of in terms of the following Pseudo code for its implementation by the worker nodes:
[Pseudo Code]

```
Receive sample from master-node
Create search term from sample
For each (genotype slot in search-term)
    For each (genotype-slot in database)
        If (genotypes match)
            Store match
                Add all codes to collection
            EndIf
    EndFor
Endfor
Maintain stored matches in memory for next stage
Return collection.length to master-node
```

As a result of these operations, the worker nodes each generate a match list of their own, a locus specific match list. The worker nodes keep a record of their own locus specific match list and send a copy of it to the master node. In the next sub-stage, the master node works upon the set of locus specific match lists it has received.

Further Benefits and Details of the Established Match Review Sub-Stage

Having obtained the set of locus specific match lists, the method proceeds to establish which of those matches are true across the different loci.

The comparison of the locus specific match lists can be parallelised to an extent, as it is possible to start the comparison once two locus specific match lists have been received; without having to wait for all the locus specific match lists to be received.

The master node coordinates which of the locus specific match lists are to be considered by which worker nodes. The master node is aware of the length of the locus specific match list each worker node has. Hence, it can instruct the worker node with the shortest list to send a copy to the worker node with the longest list for the process to start.

The worker node which has sent the match list, the transmitting worker node, then becomes inactive.

Once the worker node, the receiving worker node, has both its own generated match list and the locus specific match list sent to it, that worker node can work through its processing.

The worker node compares the two match lists.

If the unique code is present in both, then there is a match across both loci. That unique code is then added to a combination list; further match list.

If the unique code is only present in one of the match lists, then it is not a match across both loci and it can be discounted from further processing.

The outcome is a combination list (first further match list) of all the matches across those two loci. A note of the length of the combination list can then be sent back to the master node.

Other worker nodes can be working through other pairs of match lists to generate other combination lists (second further match lists and so). They too provide length information on their combination lists to the master node.

Once the length information on two lists is received, be they combination lists (further match lists) or match lists (which have not yet been processed), then the master node can tell the worker node with the shortest list to send a copy of that list to the worker node with the longest list.

The process is continued until all of the match lists and combination lists (further match lists) have been combined to generate a single combination list; a final match list.

This process can be thought of in terms of the following Pseudo code for its implementation by the master node:
[Pseudo Code]

```
While (not all lists have been combined)
    Master-node receives a list length from a worker node
    If (master-node already holds another list-length)
        Compare list lengths
        Send message to worker-node with the shortest list to send its
list to the worker node with the longer list-length for comparison
    Else
        Wait for a second list length to be returned
    EndIf
Endwhile
``` and by the following Pseudo code for its implementation by the worker nodes:
[Pseudo Code]

```
Worker-node searches locus-estate and creates match-list
Worker-node sends match-list.length to master-node and wait for response
While worker-node is active)
    If (response is from master-node)
        Send match-list to the worker-node specified in the master-node
response
        Worker-node becomes inactive
    Else
        Compare local match-list with the match-list received in the
response creating a combined list
        Worker-node sends combined-list.length to master and wait for
response
    EndIf
Endwhile
```

Further Benefits and Details of the Process Outcome Sub-Stage

The outcome list represents those unique codes which link to stored samples, in terms of their genotypes and/or profiles, which are a match with the test result across all loci present.

For each of those unique codes, it is then possible to use the associated probability information to assign a probability for that genotype and/or profile being the one which matches the test sample. The matches can then be ranked according to the probability to give a ranked list of matches. Some matches may be more likely than others, on the basis that a genotype is a match, but the occurrences/circumstances which give rise to that genotype are more or less unlikely.

Where the test result itself is a mixture, then the matches will reflect both the genotype and/or profile of the test result and that of the stored results, with the probability being a combination of both.

The invention claimed is:

1. A forensic analysis apparatus comprising at least one processor and at least one memory including computer program code, the at least one memory and the computer program code configured to, with the at least one processor, enable the apparatus at least to:

compare at least one entry of one or more test result databases against at least one entry of one or more corresponding stored result databases to identify a match, wherein the entries of each test result database comprise predetermined allele identity values associated with a different respective allele location in the DNA of a test sample, and the entries of each corresponding stored result database comprise predetermined allele identity values associated with the same respective allele location in the DNA of another sample, the test and other samples each obtained from one or more DNA sources, wherein the allele identity values for each location are stored in a different respective database, wherein the identification of a match between the entries of the one or more test result databases and the entries of the one or more corresponding stored result databases provides an indication of a potential match between at least one DNA source of the test sample and at least one DNA source of the other sample, wherein the test result and corresponding stored result databases comprise one or more possible genotypes together with respective predetermined probability information, the predetermined probability information providing an indication of the probability of the respective genotype being associated with the allele identity values to facilitate identification of a potential match between at least one DNA source of the test sample and at least one DNA source of the other sample, and wherein the apparatus is configured to identify at least one DNA source of the test sample as a potential match with at least one DNA source of the other sample based on at least one genotype of the one or more test result databases matching at least one genotype of the one or more corresponding stored result databases in combination with the respective predetermined probability information.

2. The apparatus of claim 1, wherein the apparatus is configured to:

compare at least one entry of a plurality of test result databases against at least one entry of a plurality of corresponding stored result databases to produce a respective match list for each allele location in the DNA; and compare the match lists to identify one or more allele identity values which are common to all allele locations, the identification of one or more common allele identity values indicating a greater likelihood of a potential match between at least one DNA source of the test sample and at least one DNA source of the other sample.

3. The apparatus of claim 1, wherein the test result and corresponding stored result databases comprise predetermined identification information associated with each allele identity value, the predetermined identification information linking one or more DNA sources with the allele identity value to facilitate identification of a potential match between at least one DNA source of the test sample and at least one DNA source of the other sample.

4. The apparatus of claim 1, wherein the apparatus is configured to list the one or more potentially matching DNA sources in order of probability based on the predetermined probability information associated with the identity values.

5. The apparatus of claim 1, wherein the apparatus is configured to generate one or more of the test result databases and the corresponding stored result databases using the allele identity values associated with each of the respective allele locations.

6. The apparatus of claim 5, wherein the apparatus comprises a plurality of processors configured to generate the databases associated with each of the different allele locations, and/or compare the allele identity values associated with each of the different allele locations, in parallel.

7. The apparatus of claim 6, wherein each processor is associated with a different respective allele location.

8. The apparatus of claim 3, wherein the predetermined identification information associated with each allele identity value comprises one or more of a unique code and a profile linking the one or more DNA sources to the allele identity value.

9. The apparatus of claim 2, wherein the apparatus comprises first and second processors each configured to compare at least one entry of a respective test result database against at least one entry of a corresponding stored result database to produce a respective match list for the associated allele location in the DNA, and wherein the processor with the longer match list is further configured to compare the match lists produced by the first and second processors to identify one or more allele identity values which are common to both locations.

10. The apparatus of claim 1, wherein the apparatus is configured to compare at least one entry of one or more subsequent result databases against at least one entry of the one or more corresponding stored result databases to confirm a potential match between at least one DNA source of the test sample and at least one DNA source of the other sample, the one or more subsequent result databases generated using a subsequent sample obtained from the same one or more DNA sources as the test sample.

11. A computer-implemented forensic analysis method comprising:
    comparing at least one entry of one or more test result databases against at least one entry of one or more corresponding stored result databases to identify a match,
    wherein the entries of each test result database comprise predetermined allele identity values associated with a different respective allele location in the DNA of a test sample, and the entries of each corresponding stored result database comprise predetermined allele identity values associated with the same respective allele location in the DNA of another sample, the test and other samples each obtained from one or more DNA sources, wherein the allele identity values for each location are stored in a different respective database,
    wherein the identification of a match between the entries of the one or more test result databases and the entries of the one or more corresponding stored result databases provides an indication of a potential match between at least one DNA source of the test sample and at least one DNA source of the other sample;
    wherein the test result and corresponding stored result databases comprise one or more possible genotypes together with respective predetermined probability information, the predetermined probability information providing an indication of the probability of the respective genotype being associated with the allele identity values to facilitate identification of a potential match between at least one DNA source of the test sample and at least one DNA source of the other sample, and
    wherein the apparatus is configured to identify at least one DNA source of the test sample as a potential match with at least one DNA source of the other sample based on at least one genotype of the one or more test result databases matching at least one genotype of the one or more corresponding stored result databases in combination with the respective predetermined probability information.

12. A forensic analysis computer program comprising computer code configured to perform the computer-implemented forensic analysis method of claim 11.

* * * * *